(12) United States Patent
Schumacher et al.

(10) Patent No.: US 9,028,216 B2
(45) Date of Patent: May 12, 2015

(54) ROTOR FOR AN AXIAL FLOW PUMP FOR CONVEYING A FLUID

(75) Inventors: Joerg Schumacher, Teltow (DE); Daniel Roehn, Berlin (DE)

(73) Assignee: ECP Entwicklungsgesellschaft mbH, Berlin (DE)

( * ) Notice: Subject to any disclaimer, the term of this patent is extended or adjusted under 35 U.S.C. 154(b) by 528 days.

(21) Appl. No.: 13/261,206

(22) PCT Filed: Sep. 22, 2010

(86) PCT No.: PCT/EP2010/005866
§ 371 (c)(1),
(2), (4) Date: May 17, 2012

(87) PCT Pub. No.: WO2011/035926
PCT Pub. Date: Mar. 31, 2011

(65) Prior Publication Data
US 2012/0237357 A1 Sep. 20, 2012

Related U.S. Application Data

(60) Provisional application No. 61/244,600, filed on Sep. 22, 2009.

(30) Foreign Application Priority Data

Sep. 22, 2009 (EP) .................... 09075440

(51) Int. Cl.
*A61M 1/10* (2006.01)
*F04D 29/18* (2006.01)
*F04D 29/24* (2006.01)

(52) U.S. Cl.
CPC ....... *A61M 1/101* (2013.01); *A61M 2205/0266* (2013.01); *F04D 29/181* (2013.01); *F04D 29/247* (2013.01); *A61M 1/1024* (2013.01)

(58) Field of Classification Search
USPC .......... 416/142, 143, 176, 225, 227 R, 231 R, 416/231 A, 231 B
See application file for complete search history.

(56) References Cited

U.S. PATENT DOCUMENTS

| 3,510,229 A | 5/1970 | Smith et al. |
| 3,568,659 A | 3/1971 | Karnegis |
| 3,802,551 A | 4/1974 | Somers |
| 3,812,812 A | 5/1974 | Hurwitz |
| 4,014,317 A | 3/1977 | Bruno |
| 4,207,028 A | 6/1980 | Ridder |
| 4,559,951 A | 12/1985 | Dahl et al. |

(Continued)

FOREIGN PATENT DOCUMENTS

| CA | 1008330 A1 | 4/1977 |
| CA | 2311977 A1 | 12/2000 |

(Continued)

*Primary Examiner* — Nathaniel Wiehe
*Assistant Examiner* — Kayla McCaffrey
(74) *Attorney, Agent, or Firm* — Marshall & Melhorn, LLC

(57) ABSTRACT

The invention relates to a rotor for an axial flow pump for conveying a fluid having an axis of rotation and having an impeller blade which has at least one part surface which extends transversely to the axis of rotation and beyond it, wherein the impeller blade has throughgoing webs or a network of webs which connect a different marginal regions of the impeller blades to one another. A good compressibility is hereby achieved in the radial direction with high stability during operation.

18 Claims, 7 Drawing Sheets

(56) References Cited

U.S. PATENT DOCUMENTS

| | | |
|---|---|---|
| 4,563,181 A | 1/1986 | Wijayarathna et al. |
| 4,679,558 A | 7/1987 | Kensey et al. |
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,163,910 A | 11/1992 | Schwartz et al. |
| 5,169,378 A | 12/1992 | Figuera |
| 5,181,868 A | 1/1993 | Gabriel |
| 5,183,384 A | 2/1993 | Trumbly |
| 5,191,888 A | 3/1993 | Palmer et al. |
| 5,201,679 A | 4/1993 | Velte, Jr. et al. |
| 5,275,580 A | 1/1994 | Yamazaki |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,851,174 A | 12/1998 | Jarvik et al. |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Schmitz-Rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,719,791 B1 | 4/2004 | Nusser |
| 6,860,713 B2 | 3/2005 | Hoover |
| 6,945,977 B2 | 9/2005 | Demarais et al. |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | McBride et al. |
| 7,467,929 B2 | 12/2008 | Nusser et al. |
| 7,731,675 B2 | 6/2010 | Aboul-Hosn et al. |
| 7,841,976 B2 | 11/2010 | McBride et al. |
| 7,927,068 B2 | 4/2011 | Mcbride et al. |
| 7,934,909 B2 | 5/2011 | Neusser et al. |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | Krivoruchko |
| 2004/0215228 A1 | 10/2004 | Simpson et al. |
| 2006/0008349 A1 | 1/2006 | Khaw |
| 2006/0062672 A1 | 3/2006 | McBride et al. |
| 2006/0195004 A1 | 8/2006 | Jarvik |
| 2008/0132747 A1 | 6/2008 | Shifflette |
| 2008/0262584 A1 | 10/2008 | Bottomley et al. |
| 2008/0292478 A1 | 11/2008 | Baykut et al. |
| 2008/0306327 A1 | 12/2008 | Shifflette |
| 2009/0060743 A1 | 3/2009 | McBride et al. |
| 2009/0093764 A1 | 4/2009 | Pfeffer et al. |
| 2009/0093796 A1 | 4/2009 | Pfeffer et al. |
| 2010/0041939 A1 | 2/2010 | Siess |
| 2010/0268017 A1 | 10/2010 | Siess |
| 2011/0071338 A1 | 3/2011 | McBride et al. |
| 2011/0236210 A1 | 9/2011 | McBride et al. |
| 2011/0238172 A1 | 9/2011 | Akdis |
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner |
| 2013/0204362 A1 | 8/2013 | Toellner |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 A1 | 4/2009 |
| CA | 2701810 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 19535781 A1 | 3/1997 |
| DE | 19711935 A1 | 4/1998 |
| DE | 69407869 T2 | 4/1998 |
| DE | 29804046 U1 | 6/1998 |
| DE | 69017784 T3 | 4/2000 |
| DE | 69427390 T2 | 9/2001 |
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102010011998 A1 | 9/2010 |
| EP | 0480102 A1 | 4/1992 |
| EP | 0560000 A2 | 9/1993 |

(56) References Cited

FOREIGN PATENT DOCUMENTS

| | | | |
|---|---|---|---|
| EP | 0629412 | B1 | 1/1998 |
| EP | 0884064 | A2 | 12/1998 |
| EP | 0916359 | A1 | 5/1999 |
| EP | 1066851 | A1 | 1/2001 |
| EP | 0914171 | B1 | 10/2001 |
| EP | 0768091 | B1 | 7/2003 |
| EP | 0951302 | B1 | 9/2004 |
| EP | 1114648 | B1 | 9/2005 |
| EP | 1019117 | B1 | 11/2006 |
| EP | 1 738 783 | A1 | 1/2007 |
| EP | 1337288 | B1 | 3/2008 |
| EP | 2 047 873 | A1 | 4/2009 |
| EP | 2218469 | A1 | 8/2010 |
| EP | 2229965 | A1 | 9/2010 |
| EP | 2301598 | A1 | 3/2011 |
| EP | 2308524 | A1 | 4/2011 |
| EP | 2343091 | A1 | 7/2011 |
| EP | 2345440 | A1 | 7/2011 |
| EP | 2366412 | A2 | 9/2011 |
| EP | 1651290 | B1 | 1/2012 |
| EP | 2497521 | A1 | 9/2012 |
| EP | 2606919 | A1 | 6/2013 |
| EP | 2606920 | A1 | 6/2013 |
| EP | 2607712 | A1 | 6/2013 |
| GB | 2239675 | A | 7/1991 |
| RU | 2229899 | C2 | 6/2004 |
| WO | 9202263 | A1 | 2/1992 |
| WO | 9302732 | A1 | 2/1993 |
| WO | 9303786 | A1 | 3/1993 |
| WO | 9314805 | A1 | 8/1993 |
| WO | 9401148 | A1 | 1/1994 |
| WO | 9405347 | A1 | 3/1994 |
| WO | 9409835 | A1 | 5/1994 |
| WO | 9420165 | A2 | 9/1994 |
| WO | 9523000 | A2 | 8/1995 |
| WO | 9618358 | A1 | 6/1996 |
| WO | 9625969 | A2 | 8/1996 |
| WO | 9744071 | A1 | 11/1997 |
| WO | 9853864 | A1 | 12/1998 |
| WO | 9919017 | A1 | 4/1999 |
| WO | WO 99/44651 | A1 | 9/1999 |
| WO | 0027446 | A1 | 5/2000 |
| WO | 0043054 | A2 | 7/2000 |
| WO | 0062842 | 1 | 10/2000 |
| WO | 0107760 | A1 | 2/2001 |
| WO | 0107787 | A1 | 2/2001 |
| WO | 0183016 | A2 | 11/2001 |
| WO | 03057013 | A2 | 7/2003 |
| WO | 03103745 | A2 | 12/2003 |
| WO | 2005002646 | A1 | 1/2005 |
| WO | 2005016416 | A1 | 2/2005 |
| WO | 2005021078 | A1 | 3/2005 |
| WO | 2005030316 | A1 | 4/2005 |
| WO | 2005032620 | A1 | 4/2005 |
| WO | 2005081681 | A2 | 9/2005 |
| WO | 2006020942 | A1 | 2/2006 |
| WO | 2006034158 | A2 | 3/2006 |
| WO | 2006133209 | A1 | 12/2006 |
| WO | 2007003351 | A1 | 1/2007 |
| WO | 2007103390 | A2 | 9/2007 |
| WO | 2007103464 | A2 | 9/2007 |
| WO | 2007112033 | A2 | 10/2007 |
| WO | 2008017289 | A2 | 2/2008 |
| WO | 2008034068 | A2 | 3/2008 |
| WO | 2008054699 | A2 | 5/2008 |
| WO | 2008106103 | A1 | 9/2008 |
| WO | 2008116765 | A2 | 10/2008 |
| WO | 2008124696 | A1 | 10/2008 |
| WO | 2008137352 | A1 | 11/2008 |
| WO | 2008137353 | A1 | 11/2008 |
| WO | 2009015784 | A1 | 2/2009 |
| WO | 2010133567 | A1 | 11/2010 |
| WO | 2013034547 | A1 | 3/2013 |
| WO | 2013092971 | A1 | 6/2013 |
| WO | 2013093001 | A2 | 6/2013 |
| WO | 2013093058 | A1 | 6/2013 |

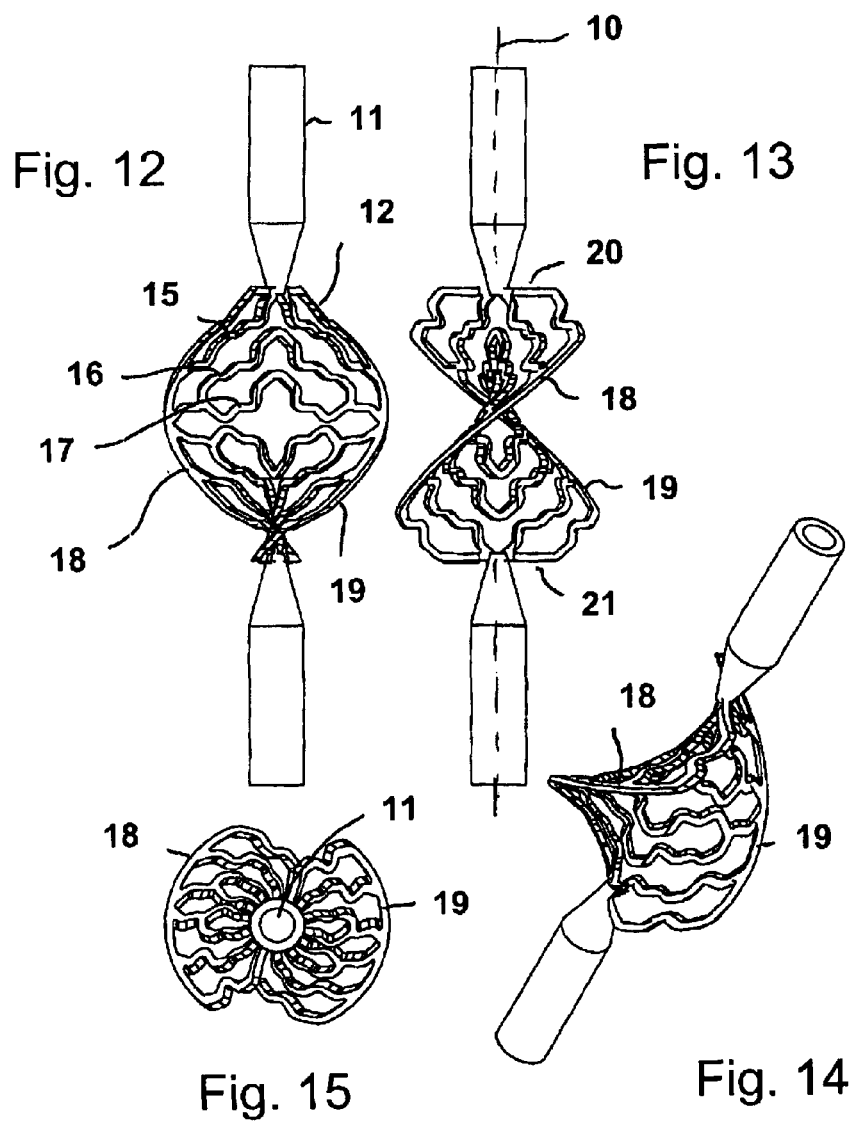

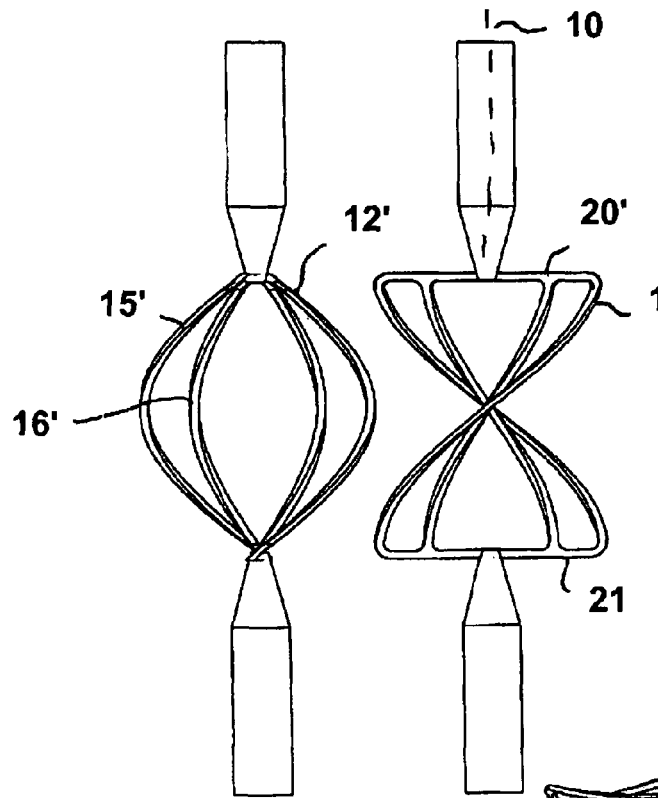
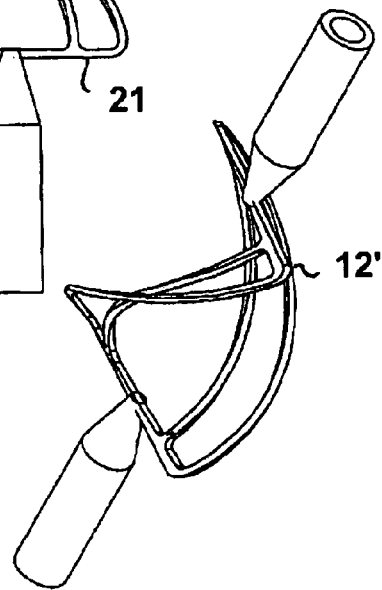
Fig. 16  Fig. 17
Fig. 19  Fig. 18

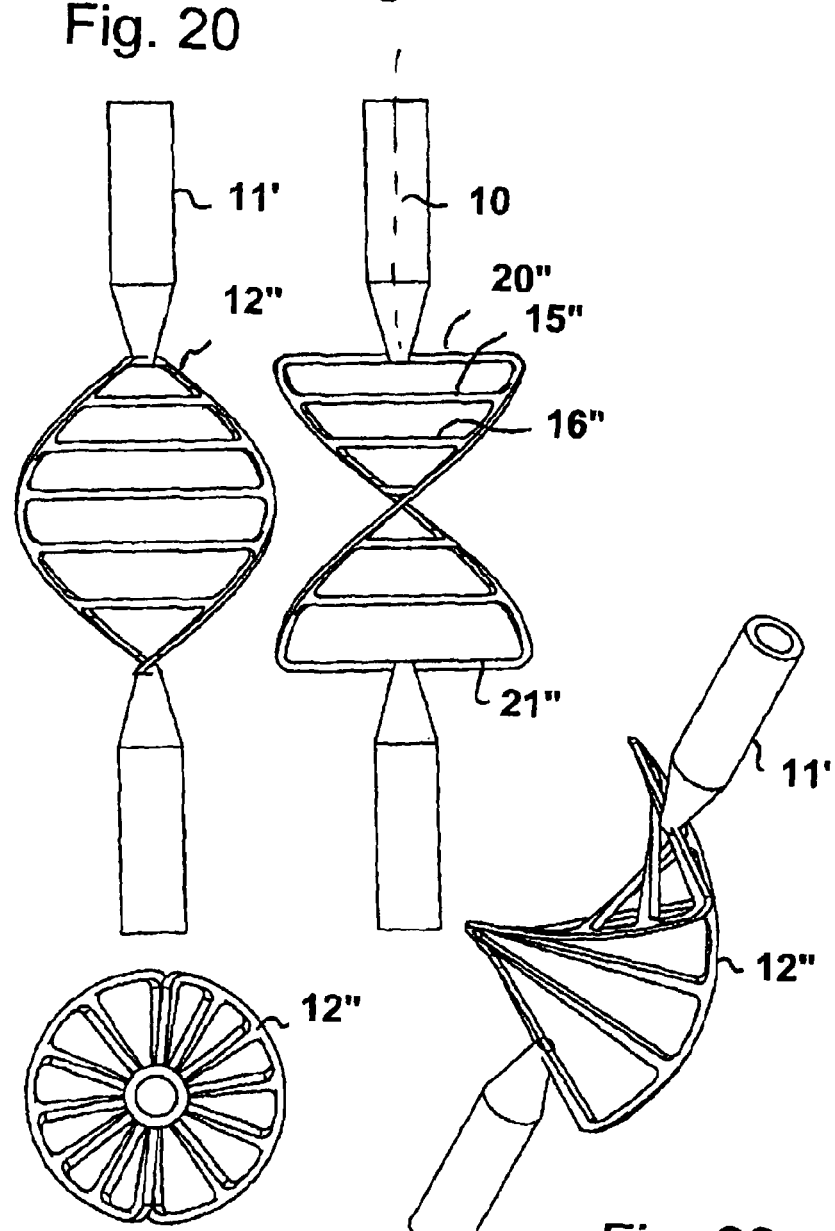

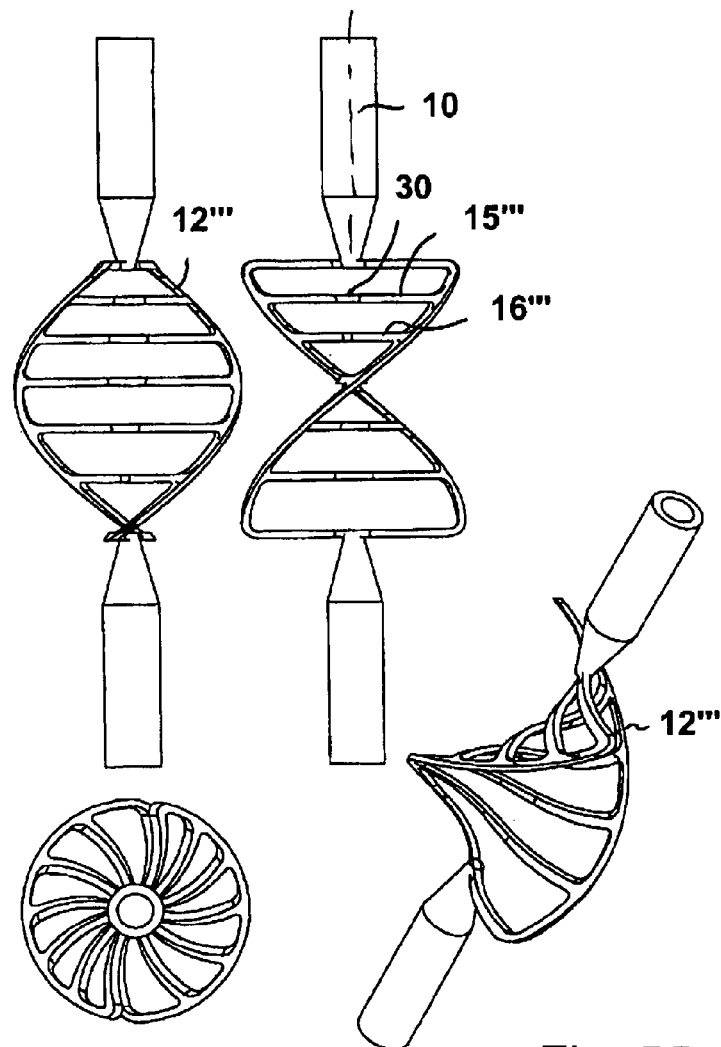

ROTOR FOR AN AXIAL FLOW PUMP FOR CONVEYING A FLUID

BACKGROUND OF THE INVENTION

The invention is in the field of mechanical engineering, in particular fine mechanics, and can be used particularly profitably in the medical field.

The invention more specifically relates to a rotor for an axial flow pump.

In particular in medical engineering, pumps are required in small construction shapes, so-called micropumps, for a variety of applications. They are used for microinvasive applications, for example for conveying the body's own fluids in the body's own cavities or vessels. Such pumps are typically connected in microconstruction to catheters and are introduced, for example, through the body's own vessels and are brought to the site of use. A specific example for the use of such pumps is represented by so-called heart pumps which can be introduced into the body through a large blood vessel and which can assist or even replace the blood conveying of the heart.

Rotary pumps have specifically become known in this connection which are made as axial flow pumps.

A specific property of some pumps of this type is, in addition to their small construction shape per se, furthermore the radial compressibility so that such a pump can be compressed for transport through a blood vessel and can be expanded after the conveying to the site of use, for example in a heart chamber.

A pump of this type has become known, for example, from the US laying-open publications US 2009/0060743 A1 and US 2008/0114339 A1. The axial flow pumps described in these documents each have a shaft and a row of impeller blades flexibly attached thereto which convey a fluid in an axial direction on a rotation of the shaft. The impeller blades can be radially applied to the shaft so that the rotor is compressible in this manner. In operation, the individual impeller blades become erect, inter alia due to the fluid counterpressure, so that the pump has a considerable conveying capacity.

BRIEF SUMMARY OF THE INVENTION

It is the underlying object of the invention against the background of the prior art to provide a rotor for an axial flow pump which can be built as simply as possible and which can be manufactured inexpensively. It should moreover be low in mass and allow a sufficient conveying capacity.

The rotor in accordance with the invention has an impeller blade having at least one part surface which extends transversely to and beyond the axis of rotation, with the impeller blade having webs which each connect, individually or as a network, different marginal regions of the impeller blade to one another.

In accordance with the invention, a rotor is understood as a "compressible rotor" in the sense of the claims which is radially compressible. This preferably means that the rotor can adopt a compressed state (e.g. on the introduction into a human body or animal's body) as well as an expandable state (in pump operation, preferably in the body, e.g. in a left heart ventricle). In this respect, in the expanded state, the largest radial dimension of the rotor (that is e.g. the outer diameter of the rotor) is preferably at least 10%, particularly preferably at least 25%, larger than in a compressed state (the percentage figures relate to the dimension in the expanded state). The changing from the compressed state into the expanded state (and back) is preferably possible in a reversible manner as desired, i.e. without rotor damage.

This can mean, for example, that at least one part surface of the impeller blade is designed such that elements of the part surface are disposed opposite one another with respect to the axis of rotation at the same axial position on different sides of the axis of rotation. This can be realized, for example, such that the axis of rotation passes through the part surface and is radially surrounded at a plurality of sides by elements of the part surface.

This example can also be described such that the part surface can inscribe a circle which the axis of rotation passes through centrally.

In this respect, the impeller blade has throughgoing webs or a network of webs which connect further webs which each form a marginal section of the impeller blade at least regionally, in different marginal regions of the impeller blade, which can also be called marginal sections, and thus span the impeller blade. Webs of this type are suitable, in particular together with optionally provided marginal strips of the impeller blade, to span said impeller blade and to allow a fastening of a film which forms the conveying surface of the impeller blade and is supported by the webs. A very light construction of the impeller blade is thus implemented which nevertheless allows the creation of a large conveying surface.

The webs and the further webs can advantageously be made in one piece from a common base body. They can respectively have the same or different cross-sections.

The impeller blade is advantageously designed as neckless and is implemented in a self-supporting manner.

This means that the torque along the rotor is transferred by means of the impeller blade surface, that is, of the flat, curved body which essentially forms the impeller blade. Since the neck usually provided for transferring the torque and for holding the impeller blade surface has a substantial volume which can be saved by the design in accordance with the invention, a substantially greater compressibility of the rotor can be achieved in accordance with the invention.

At least one of the webs can connect two marginal regions of the impeller blade which are disposed opposite one another radially with respect to the axis of rotation.

Provision can, however, also be made that at least one web connects two marginal regions of the impeller blade which are disposed opposite one another in the longitudinal direction of the axis of rotation.

The total surface of the impeller blade can in any case be divided by webs in accordance with a desired pattern to crate the desired impeller blade surface which is formed either by the webs itself or by a film spanned over the webs. The webs, just like the conveying surface of the impeller blade, do not have to extend in a plane, but can rather describe a three-dimensional surface, for example extending as a screw helix. In this respect, the webs can extend contact-free next to one another or also be connected to one another spot-wise at intersections of the impeller blade, for example at such spots which are exposed to a special mechanical stress.

Such intersections can, however, also be selected such that a folding of the webs on a compression movement or an expansion movement of the impeller blade is made possible or facilitated by them.

At least some of the intersections, in particular all the intersections, can be spaced apart from the axis of rotation of the impeller blade. At least some webs, in particular all of the webs, can be spaced apart from the axis of rotation over their total length.

To design the webs as correspondingly compressible or expandable, they can advantageously be designed in meandering form. The meandering structure is advantageously applied in the surface of the impeller blade.

To create a corresponding mechanism for the compression and expansion of the impeller blade, provision can advantageously be made that the webs comprise a shape memory alloy, for example nitinol. In this case, a respective desired design of the impeller blade can be aimed for by temperature change. The mechanism of compression can here also be supported by utilization of the hyperelastic properties of the material nitinol.

If marginal sections of the impeller blade are made as marginal strips or marginal webs, they can additionally stabilize the impeller blade and can form a reliable hold or a support for a corresponding impeller blade film together with the webs. A film of this type can then be fastened to the webs and to the marginal strips or parts of the marginal strips, for example, by adhesive bonding.

The impeller blade can be arranged in full within a hollow-cylindrical component and can be connected to it in marginal regions. The hollow cylinder can be connected to one or two rotatably journalled drive journals in the region of the axial end regions of the impeller blade. The impeller blade is advantageously radially compressible together with the hollow-cylindrical component.

The invention also relates to a rotor for an axial flow pump for conveying a fluid having an axis of rotation and having an impeller blade which is designed neckless as a body which is flat with respect to its contour and which is rotated spirally about an axis.

This type of construction allows a particularly simple manufacture and can be compressed particularly simply and to a particularly small dimension, in particular in that no neck is required. This is decisive for the introduction of the rotor for medical applications via the bloodstream in the body of a human.

The impeller blade is advantageously made as a lattice or as a network of webs from a planar metal sheet.

This allows an inexpensive mass production with conventional methods of sheet metal working.

Provision can specifically advantageously be made that the impeller blade is in particular manufactured from a nitinol metal sheet, by cutting out of the webs, in particular by water cutting, laser cutting or electric erosion.

The webs can in this respect be made in meandering form in the sheet metal plane and/or perpendicular thereto. An easy bendability thereby results in the compression of the rotor in the radial direction.

Furthermore, the webs can have a different area moment of inertia in the sheet metal plane than perpendicular thereto.

A substantially smaller resistance can thereby be realized with respect to a radial compression of the impeller blade than with respect to loads which act on the impeller blade by the pumping operation. Loads which arise by a fluid pressure against the impeller blade plane are thus taken up in a very much stiffer manner.

A particularly simple embodiment of an impeller blade in accordance with the invention provides that said impeller blade is made as an elongate body, in particular a rectangular body, which is rotated spirally about an axis, in particular its central longitudinal axis. In this respect, the spiral form can also be designed in an irregular manner with respect to the pitch or, optionally, also otherwise distorted.

The rotation axis of the body preferably lies substantially parallel to the axis of rotation or corresponds to it on the assembly of the rotor.

A symmetrical helical design, or a spiral design asymmetrical to a limited extent, of an impeller blade thus results, for example, in that the ends of a planar rectangle area rotated against one another by 180 degrees or by a different angular amount about the longitudinal axis. The impeller blade surface is then made as a single, contiguous surface which extends beyond the axis of rotation and is passed through by it. The surface can in this respect also have cut-outs, for example in the region of the axis of rotation.

Such an impeller blade can be made self-supporting on a correspondingly stable design of the webs and rims so that the torque can, for example, be transferred via the impeller blade alone and no neck is required. The stiffness of the impeller blade itself is sufficient for the conveying of the fluid when it is driven from one of its ends. The torque is then introduced via the end-face rim of the impeller blade.

Provision can, however, also advantageously be made that the impeller blade is connected to a hollow cylindrical component surrounding said impeller blade. Such a hollow cylindrical component can be provided, for example, as a ring or as a tube section which additionally stabilizes the impeller blade and can be manufactured in one piece with it. A plurality of rings spaced apart coaxially and axially can, however, also be connected to the impeller blade at the periphery of the rotor.

These rings can then be spaced apart from one another axially by webs and can be made as radially compressible to be able to be compressed together with the impeller blade for the purpose of introduction into a body.

The present invention allows the simplest manufacture of an impeller blade for an axial flow pump in which the rims and reinforcement webs of the impeller blade can be manufactured, for example, in one piece by injection molding or machining of a metal sheet and can be provided with a film. Sections correspondingly axially adjoining the impeller blade can also be manufactured in one piece with the impeller blade to allow a rotatable journalling axially subsequent to the impeller blade and the introduction of a torque.

BRIEF DESCRIPTION OF THE DRAWINGS

The invention will be shown and subsequently described in the following with reference to an embodiment in a drawing. There are shown FIG. 1 an overview in section across an intracardiac catheter having an axial flow pump introduced into a heart chamber;

FIG. 3 the impeller blade of FIG. 2, with invisible contours being drawn in;

FIG. 8 the view of FIG. 7 with invisible contours drawn in; and

FIG. 12 a side view of a rotor with meandering-shape or wavy webs which span the impeller blade;

FIG. 13 the impeller blade of FIG. 12 in a view rotated by 90 degrees;

FIG. 14 the impeller blade of FIG. 12 in a three-dimensional view;

FIG. 15 the impeller blade of FIG. 12 in an axial plan view;

FIG. 16 another variant of an impeller blade with webs extending substantially in the direction of the axis of rotation in a side view;

FIG. 17 the arrangement of FIG. 16 in a side view rotated by 90 degrees;

FIG. 18 the arrangement of FIG. 16 in a three-dimensional view;

FIG. 19 the arrangement of FIG. 16 in an axial plan view;

FIG. 20 a further embodiment of a rotor with webs extending straight transversely to the axis of rotation in a side view;

FIG. 21 the arrangement of FIG. 20 in a side view rotated by 90 degrees;

FIG. 22 the arrangement of FIG. 20 in a three-dimensional view;

FIG. 23 the arrangement of FIG. 20 in an axial plan view;

FIG. 24 a further embodiment of a rotor with curved webs extending transversely to the axis of rotation in a side view;

FIG. 25 the embodiment of FIG. 24 in a side view rotated by 90 degrees;

FIG. 26 the embodiment in accordance with FIG. 24 in a three-dimensional view; and FIG. 27 a plan view of the arrangement in accordance with FIG. 24 in an axial direction.

DETAILED DESCRIPTION OF THE INVENTION

Figure 1:
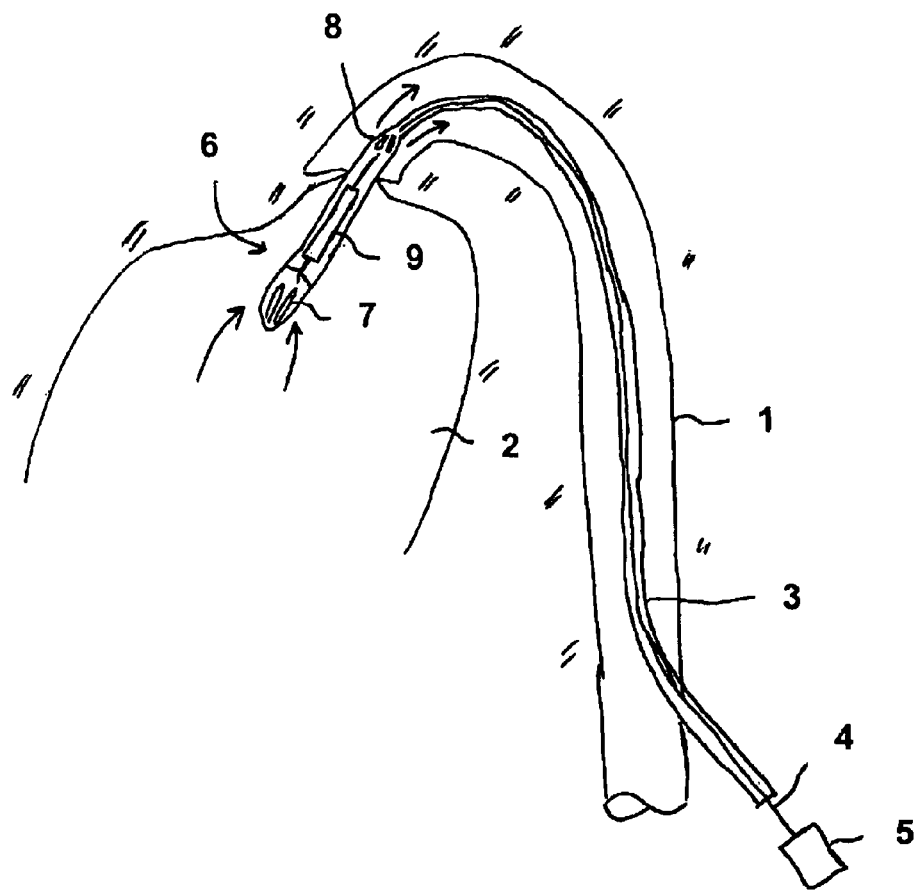

FIG. 1 schematically shows a blood vessel 1 in a human body which ends in a heart chamber 2 and into which a hollow catheter 3 is introduced.

A drivable shaft 4 runs through the hollow catheter 3 and can be driven at high speed by a motor 5 arranged outside the body. The hollow catheter 3 can be filled with a biocompatible fluid which can serve, on the one hand, the reduction in the friction of the shaft and, on the other hand, the dissipation of heat.

A heart pump 6 is arranged at the end of the hollow catheter 3 which sucks in blood through first openings 7 within the heart chamber 2 and emits it again via second openings 8 within the blood vessel 1. The pump 6 in this manner assists the pumping activity of the heart or replaces it.

A rotor 9 is shown schematically in the interior of the pump 6 and rotates, driven by the shaft 4, about its longitudinal axis and conveys the blood in the axial direction from the heart chamber 2 toward the blood vessel 1. Such an axial flow pump is typically provided with a housing and with a rotor having conveying impellers journalled therein.

Such heart pumps are already known in different construction forms, with in particular the radial compressibility of such pumps playing a large role for its performance capability. The pumps should be able to be introduced through the blood vessel 1 in compressed form and thereupon be expandable so that the conveying impellers can convey the blood with conveying surfaces which are as large as possible and in a sufficiently large flow cross-section. For this purpose, different rotor designs with foldable rotors and housings are already known. The rotor in accordance with the invention will be described in more detail with reference to the following Figures.

Figure 2:
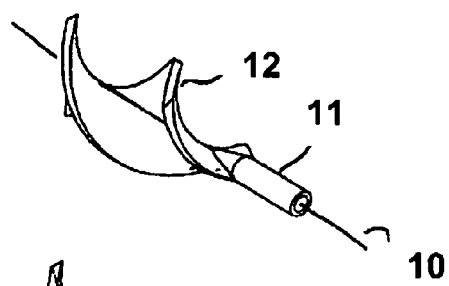
FIG. 2 an impeller blade of an axial flow pump in a three-dimensional view.

FIG. 2 for this purpose first shows an embodiment of a one-piece impeller blade which is rotated spirally about an axis of rotation 10. A shaft 11 is provided which axially adjoins the impeller blade 12, but does not pass through it. The impeller blade 12 is in this respect self-supporting and transfers the torque without a neck being necessary.

The impeller blade 12 can be manufactured in one piece with the shaft root 11 and, optionally, with a further shaft root on the axially oppositely disposed side of the impeller blade 12, for example, from plastic in an injection molding process.

FIG. 2 schematically shows the outer shape of the impeller blade 12 without looking more closely at the inner structure. This will be described more exactly within the framework of the invention with reference to Figures following further below.

Figure 3:
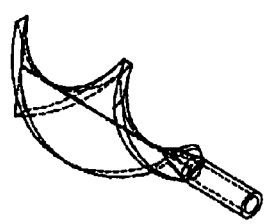
Figure 4:
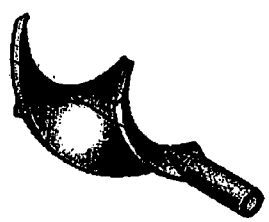
FIG. 4 the impeller blade of FIG. 2 with an emphasis of the visible surface by hatching.

FIG. 3 shows the impeller blade of FIG. 2 from the same perspective, with, however, lines invisible per se being shown in dashed form. FIG. 4 shows a representation in which the three-dimensional shape is shown more plastically with reference to hatching.

Figure 5:
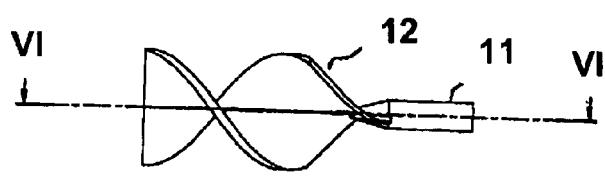
FIG. 5 a side view of the impeller blade of FIG. 2.
Figure 6:
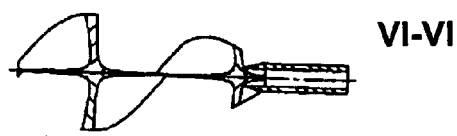
FIG. 6 a section of the view of FIG. 5.

FIG. 5 shows a side view of the impeller blade 12 and of the shaft root 11, with a section being indicated by VI which is shown in more detail in FIG. 6.

Figure 7:
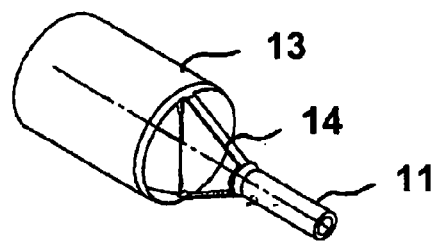
FIG. 7 an embodiment of a rotor of an axial flow pump in a three-dimensional view.

FIG. 7 shows another embodiment of a rotor, in which the impeller blade 12 is surrounded by a tubular support device or envelope to which it is rigidly connected in this embodiment so that the tubular envelope or support device 13 rotates with the impeller blade 12. The envelope is connected to the shaft root 11 by means of a fork-like holder 14. The holder can also be made as a spatially rotated triangular plate which can be directly connected to the end of the impeller blade 12. The envelope is advantageously compressible and expandable and provides a hold for the impeller blade 12. The envelope 13 can, for example, comprise a plastic tube piece which can be surrounded by a wire meshwork for support. The wire meshwork can also comprise a shape memory material so that it can support the sleeve 13 via a shape change. In particular in the case that the impeller blade 12 is made neckless and is stabilized in a self-supporting manner, it can be connected to the inner sides of the sleeve 13 and can be spanned by its expansion movement.

Figure 8:
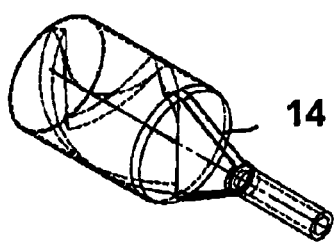
Figure 9:
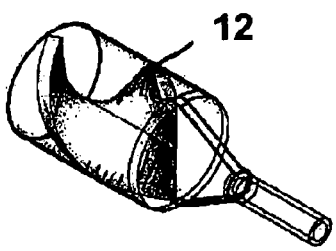
FIG. 9 a partly broken away view of the arrangement of FIG. 7.

FIG. 8 shows the view of FIG. 7, with lines invisible per se being drawn in dashed form, and FIG. 9 shows a three-dimensional representation of the impeller blade 12, with the shape being emphasized by hatching.

Figure 10:
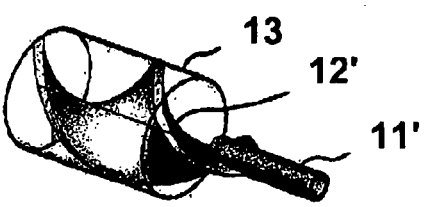
FIG. 10 a further rotor in which the fastening of a drive shaft is solved differently than in the embodiment in accordance with FIG. 7.

FIG. 10 shows as a further variant an impeller blade 12' which is surrounded by a sleeve 13 and which has a shaft root 11' integrated into its shape which is per se not connected to the sleeve 13.

Figure 11:
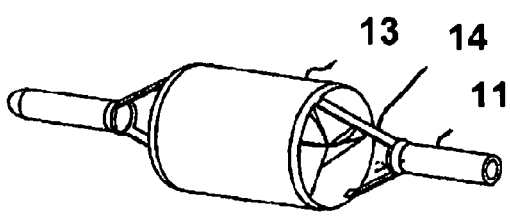
FIG. 11 a rotor with two shaft roots fastened at both sides.

FIG. 11 shows an embodiment of a sleeve 13 with two shaft roots 11 at both sides which are each connected via a fork-like holder 14 to the sleeve 13, but not to the impeller blade.

As in FIGS. 2 to 10, it can also be seen here that the impeller blade can have a substantially unchanging cross-section without thickened portions; cross-sectional changes are, however, by no means precluded. Correspondingly, the torque is transferred via the areal body itself so that no neck is needed.

FIG. 12 shows the structure of a typical impeller blade 12 which is spanned by webs 15, 16, 17 in more detail. In addition, marginal strips 18, 19 are drawn in which can typically comprise the same material as the webs 15, 16, 17. The individual webs are made as wavy, with the respective wave contour in each case remaining within the impeller blade surface. The webs can thereby be spanned, and thus expanded and compressed, in the surface of the impeller blade. This wave structure moreover produces a stiffening perpendicular to the impeller blade surface.

The webs can, for example, comprise a shape memory material such as nitinol, which additionally facilitates the compression and expansion of the impeller blade 12.

The impeller blade 12 generally comprises in the example shown a substantially rectangular frame whose marginal strips 20, 21 at the end face, drawn in FIG. 13, are rotated against one another by 180 degrees about the axis of rotation 10 to form a spiral structure. A single, contiguous surface hereby results which extends radially to all sides of the axis of rotation 10 and has at every level of the axis of rotation impeller blade regions which are mutually oppositely disposed with respect to the axis of rotation 10. A high symmetry of the impeller blade with correspondingly symmetrical force distribution is hereby achieved. The starting body can generally also have different base shapes than the rectangular shape, with it being advantageous if the body later, in spiraled form, covers the cross-section of a rotor housing as much as possible and if its outer contour maps the inner contour of the housing as exactly as possible.

In the embodiment of FIGS. 12, 13, 14, 15, the shaft roots 11 can be contiguous in one piece or by a weld connection with the webs 15, 16, 17 and the marginal strips 18, 19, 20, 21 so that the total rotor can be manufactured particularly simply and inexpensively and reliable connections are present for the transfer of the torque. The frame formed from the webs 15, 16, 17 and the marginal strips 18, 19, 20, 21 is typically covered with a thin, highly flexible film which forms the actual conveying surface.

The impeller blade is connected to one or both of its axial ends in each case by a drive journal which in each case axially adjoins the impeller blade.

Due to the omission of a neck in the axial region of the impeller blade 12, the compression is facilitated, on the one hand, since the webs can deform over their total length; on the other hand, the rotor becomes flexible, whereby the introduction in compressed form along a blood vessel can be facilitated. In accordance with the described embodiment, the webs are connected at points at intersections and form a network which additionally gives the impeller blade stiffness.

FIGS. 16, 17 and 18 show a rotor in two side views and in one tree-dimensional view with an impeller blade 12' in which the individual webs 15', 16' substantially extend along the axis of rotation 10 and in this respect spirally about it. A good compressibility for the rotor hereby results in the radial direction and, with corresponding covering, a conveying surface which has only few irregularities for the fluid to be conveyed so that only relatively little damage of blood components is to be feared even at high speeds. Even at a high fluid counterpressure, which can be adopted at high rotor speeds, evasive movement of the impeller blade 12' are tightly limited by a good stabilization of the webs. In this embodiment, too, the impeller blade can be considered as a whole as a rectangular frame whose two oppositely disposed end-face marginal strips 20', 21' are rotated against one another by 180 degrees about the axis of rotation 10. The manufacture of a corresponding planar frame with parallel webs 15', 16' is particularly simple.

FIGS. 20, 21, 22 show, in two side views and in one three-dimensional view, an impeller blade 12" having two shaft journals 11', with the impeller blade having webs 15", 16" which extend horizontally transversely to the axis of rotation 10 and which are in each case straight per se, but give the impeller blade 12" as a whole the same helical structure such as is given with respect to the contour in the impeller blade in accordance with FIG. 17. In particular when the impeller blade 12" is supported by an outer envelope and is connected thereto, the webs 15", 16" of the impeller blade 12" can be particularly efficiently stretched on the expansion movement with the result of a stable impeller blade. The foil spanned between the webs and the marginal strips 20", 21" is thereby likewise stabilized so that it stands fold-free in the fluid to be conveyed.

FIG. 23 shows for this purpose an end-face view of the rotor with the webs extending beyond the axis of rotation.

FIGS. 24-27 show an embodiment similar to that shown in FIGS. 20-23, with an impeller blade 12''' whose webs 15''', 16''' extend transversely to the axis of rotation 10, with the individual webs 15''', 16''' not extending straight per se, but rather being curved in wave shape for the achieving of further improved impeller blade geometry, as required. This can, for example, be achieved by introduction of an attenuated region 30 in each case at the center of each web 15''', 16'''' which facilitates an evasion of each web from the straight direction on adoption of the shown helical shape of the impeller blade 12'''. However, it can also be achieved by a defined prebending of the webs. The advantage hereby achieved is, on the one hand, that the webs adopt a defined preferred direction on compression so that no undefined kinking loads of the webs occur on the compression. A further advantage comprises the fact that the precurved webs adopt an increasingly straight shape when they evade the fluid pressure in the operating state, which is almost unavoidable with such elastic structures. The rotor of FIGS. 24 to 27 could then, for example, adopt the shape of the rotor of FIGS. 20 to 23 in the operating state.

In this embodiment, too, as in the other above-described embodiments, the impeller blade as a whole is surrounded by marginal strips for fastening the film forming the conveying surface and for stabilizing the impeller blade.

The construction principle shown in FIGS. 12 to 26 generally allows any desired design of the webs so that extensive optimization possibilities are present here to design the pattern in accordance with the demands.

In an advantageous embodiment, in this respect, the webs are made so that only elastic deformations occur on the deformation of the rotor into the designated compressed form so that the rotor can unfold automatically into the designated uncompressed form after removal of the forces triggering the compression.

This designated uncompressed form is not necessarily the form of the rotor in the operating state since it possibly deforms further under the influence of the fluid pressure.

A particularly advantageous design of the rotor is now such that the rotor is subject only to elastic deformations under the influence of the fluid pressure and shows the ideal geometry for the application at the designated working point.

Overall, the design of the rotor of an axial flow pump in accordance with the invention having the corresponding impeller blade allows a material-saving and technically simple manufacture of the rotor which combines a good compression capability with high stability in operation.

The invention claimed is:

1. A compressible rotor for an axial flow pump for conveying a fluid having an axis of rotation and having an impeller blade which has at least one part surface which extends transversely to the axis of rotation and beyond it, wherein the impeller blade has webs which each, individually or as a network, connect one or more respective further webs forming a respective margin of the impeller blade to one another in different marginal regions of the impeller blades, wherein the connecting webs and the further webs, which form the margin of the impeller blade, comprise the same material, wherein at least one web or the network of webs connects two marginal regions of the impeller blade beyond the axis of rotation.

2. The rotor in accordance with claim 1, wherein the impeller blade is neckless.

3. The rotor in accordance with claim 1, wherein the impeller blade is self-supporting.

4. The rotor in accordance with claim 1, wherein at least one web or the network of webs connects two marginal regions of the impeller blade which are disposed mutually opposite viewed in the longitudinal direction of the axis of rotation.

5. The rotor in accordance with claim 1, wherein two or more respective webs are provided which extend parallel to one another or at a constant spacing from one another.

6. The rotor in accordance with claim 1, wherein at least one of the webs is made in meandering form.

7. The rotor in accordance with claim 1, wherein marginal regions of the impeller blade are made as marginal strips or marginal webs.

8. The rotor in accordance with claim 7, wherein the impeller blade is surrounded by a throughgoing marginal strip or a throughgoing marginal web.

9. The rotor in accordance with claim 1, wherein the impeller blade is manufactured as a lattice or as a network of webs from a planar metal sheet.

10. The rotor in accordance with claim 9, wherein the impeller blade is manufactured, in particular from a nitinol metal sheet, by cutting out the webs, in particular by water cutting, laser cutting or electric erosion.

11. The rotor in accordance with claim 10, wherein the webs are shaped in meandering form in the plane of the metal sheet and/or perpendicular thereto.

12. The rotor in accordance with claim 10, wherein the webs have a different area moment of inertia in the plane of the metal sheet than perpendicular thereto.

13. The rotor in accordance with claim 1, wherein the impeller blade is fixedly connected to a hollow cylindrical component surrounding it.

14. The rotor in accordance with claim 1, wherein a film is spanned between the webs and the margin of the impeller blade.

15. The rotor in accordance claim 1, wherein the impeller blade is compressible radially together with the hollow cylindrical component.

16. A compressible rotor for an axial flow pump for conveying a fluid having an axis of rotation and having an impeller blade which has at least one part surface which extends transversely to the axis of rotation and beyond it, wherein the impeller blade has webs which each, individually or as a network, connect one or more respective further webs forming a respective margin of the impeller blade to one another in different marginal regions of the impeller blades, wherein the connecting webs and the further webs, which form the margin of the impeller blade, comprise the same material, wherein the webs comprise a shape memory alloy.

17. A compressible rotor for an axial flow pump for conveying a fluid having an axis of rotation and having an impeller blade, wherein the impeller blade is made neckless as a body flat with respect to its contour which is spirally rotated about an axis.

18. A rotor for an axial flow pump for conveying a fluid having an axis of rotation and having an impeller blade which has at least a part surface which extends transversely to the axis of rotation and beyond it, wherein the impeller blade has webs which each, individually or as a network, connect different marginal regions of the impeller blade to one another, wherein the webs comprise a shape memory alloy.

* * * * *